United States Patent [19]

Murphy, Jr.

[11] Patent Number: 5,006,312
[45] Date of Patent: Apr. 9, 1991

[54] GRAVIMETRIC TITRATION APPARATUS FOR THE DETERMINATION OF THE IODINE NUMBER OF CARBON BLACK

[76] Inventor: Lawrence J. Murphy, Jr., 15 Lutheran Dr., Nashua, N.H. 03063

[21] Appl. No.: 539,646

[22] Filed: Jun. 18, 1990

Related U.S. Application Data

[62] Division of Ser. No. 401,347, Aug. 31, 1989.

[51] Int. Cl.$^5$ .............................................. G01N 31/16
[52] U.S. Cl. ....................................... 422/62; 422/76; 422/77; 436/51; 436/55; 436/163
[58] Field of Search ...................... 422/62, 75, 76, 77; 436/51, 124, 177, 178, 163, 908, 150, 151, 55; 204/1 T

[56] References Cited

U.S. PATENT DOCUMENTS

| | | | |
|---|---|---|---|
| 3,438,736 | 4/1969 | Jucker | 436/908 |
| 3,922,335 | 11/1975 | Jordan et al. | 422/150 |
| 4,035,336 | 7/1977 | Jordan et al. | 524/575.5 |
| 4,315,902 | 2/1982 | Dilbert | 422/150 |
| 4,715,413 | 12/1987 | Backlund et al. | 141/94 |

OTHER PUBLICATIONS

ASTM D 1510-88b, Standard Test Method for Carbon Black Iodine Adsorption Number, approved 9/30/88, published 2/1989.

*Primary Examiner*—Robert J. Hill, Jr.
*Attorney, Agent, or Firm*—David J. Koris

[57] ABSTRACT

A gravimetric method for determining the iodine adsorption number of carbon black is disclosed. The concentration of an accurately weighed iodine solution is determined by titrating with a standardized titrant and determining the concentration of the iodine solution by the weight of the standardized titrant needed to reach the titration endpoint. An appropriate amount of accurately weighed iodine solution is mixed with an accurately weighed amount of carbon black, and the mixture is equilibrated. The concentration of the resulting supernatant is determined by determining the weight of the standardized titrant needed to reach the titration endpoint. The iodine adsorption number is then determined based on the gravimetrically determined concentrations of the solutions. Preferably, the method is semi-or fully automated, and an apparatus for accomplishing the same is disclosed.

9 Claims, No Drawings

GRAVIMETRIC TITRATION APPARATUS FOR THE DETERMINATION OF THE IODINE NUMBER OF CARBON BLACK

This is a division of application Ser. No. 401,347, filed Aug. 31, 1989.

BACKGROUND OF THE INVENTION

Carbon black is an amorphous form of carbon which has varied uses, including use as a pigment and as a strengthening and reinforcing agent for many rubber products. Generally, it is commercially prepared by the partial combustion or thermal decomposition of hydrocarbons in the vapor phase.

Because of the amorphous nature of their carbon atoms, the physical properties of carbon blacks differ. The particular use of a carbon black is dependent upon these physical properties, more particularly, its chemical composition, pigment properties, surface area, state of subdivision, adsorption activity, colloidal properties, etc.

Due to the variable nature of the physical properties of carbon blacks, it is important that there is a high degree of product uniformity. One particularly useful manner of characterizing carbon black is by determining its iodine adsorption number. The iodine adsorption number is related to the surface area of carbon blacks and is generally in agreement with nitrogen surface area, although it is also affected by the presence of volatiles, surface porosity, and extractables.

During the commercial production of carbon black, it is necessary to monitor the carbon black being produced in order to ensure that the carbon black produced in the run falls within the desired specifications. This is often accomplished by taking samples and testing for the iodine adsorption number. The accuracy of the iodine number of a carbon black has become increasingly important in recent years as an aspect of quality control in the final product into which the carbon black is incorporated.

The iodine adsorption number of carbon black is commonly determined according to the industry-accepted standard volumetric test set forth in ASTM D1510.

According to this test, an adequate sample of carbon black is dried for one hour in an oven set at 125° C. Thereafter, the carbon black is weighed to the nearest 0.000 1g. Next, the sample of carbon black is treated with 25 ml of 0.0473 N iodine solution (previously standardized). The mixture is capped and shaken, and then centrifuged. The supernatant solution is decanted, and 20 ml of the supernatant solution is pipetted into a flask. This solution is titrated with 0.0394 N sodium thiosulfate solution (previously standardized). When the solution turns pale yellow, five drops of starch solution are added and the titration is continued drop wise until the endpoint (colorless solution) is reached. The titration volume is recorded to the nearest 0.25 ml if done manually, or to the nearest 0.01 ml if done via a digital buret.

A blank iodine determination is made by pipetting 20 ml or dispensing 25 ml of 0.0473 N iodine solution into a flask and titrating with 0.0394 N sodium thiosulfate.

The iodine adsorption number is calculated to the nearest 0.1 g/kg according to the equation:

$$I = [(B-S)/B] \times (V/W) \times N \times 126.91$$

where
 $I$ = iodine adsorption number, g/kg,
 $B$ = ml of sodium thiosulfate required for the blank,
 $S$ = ml of sodium thiosulfate required for the sample,
 $V$ = calibrated volume of the 25 ml iodine pipet or dispenser,
 $W$ = grams of carbon black sample, and
 $N$ = normality of the iodine solution, and
 $126.91$ = equivalent mass of iodine.

The volumetric measurements of the aforementioned method and resultant calculation of the iodine number based on the same are limited with regard to precision. For example, the volumetric measurements used to standardize the sodium thiosulfate solution are limited by the accuracy of the human eye reading the volume in a glass buret, by the sensitivity of digital buret, and by the tolerance of the volumetric equipment.

OBJECTS AND SUMMARY OF THE INVENTION

It is an object of the present invention to provide a method of determining the carbon black iodine adsorption number in which the uncertainty in the measurements are smaller than the uncertainty in state-of-the-art methods.

It is another object of the present invention to provide a method for the determination of the carbon black iodine adsorption number which provides better reproducibility within and between laboratories.

It is another object of the present invention to provide a method for reducing the variability in properties of carbon black samples by more accurately measuring the properties of the samples.

It is yet another object of the present invention to develop a method of determining the iodine number of carbon black which reduces the random error compared to current state-of-the-art analytical tests.

The above-mentioned objectives and others are accomplished by the present invention wherein the iodine number of carbon black is determined by employing gravimetric methods.

More particularly, the present invention relates to a gravimetric method for the determination of the iodine adsorption number of carbon black. In this method, the concentration of an iodine solution is determined by adding an appropriate standardized titrant to an accurately weighed aliquot of the iodine solution until a titration endpoint is reached. The concentration of the iodine solution is determined by accurately weighing the amount of the standardized titrant necessary to reach the endpoint. An appropriate amount of the iodine solution is added to a previously weighed amount of carbon black. The carbon black-iodine solution mixture is equilibrated, and the standardized titrant is added to an accurately weighed portion of the supernatant from the carbon black-iodine solution mixture until an endpoint is reached. The amount of the standardized titrant necessary to reach the endpoint is then accurately weighed in order to determine the concentration of the supernatant. The titrant is standardized by adding the titrant to an accurately weighed amount of a solution of an appropriate primary standard having a known concentration until a titration endpoint is reached. The concentration of the titrant is determined by accurately weighing the amount of the same necessary to reach the endpoint. The iodine adsorption number of the carbon black is mathematically determined based on the gravimetrically determined concentration of the primary standard solution, the titrant, the iodine blank, and the supernatant from the equilibrated carbon black-iodine solution mixture.

By "accurately weighed", it is meant that all weight measurements are measured to the nearest 0.1 mg.

The present invention also relates to an apparatus for determining the iodine adsorption number of carbon black. Preparation means for preparing the solutions to be titrated against a titrant, include a first balance for weighing iodine solutions, carbon black, an appropriate primary standard and a solution comprising the primary standard; equilibration means for equilibrating a mixture of accurately weighed carbon black and accurately weighed iodine solution. Titration means for titrating the primary standard solution, the iodine solution, and the supernatant from the equilibrated carbon black-iodine solution mixture against the titrant comprise a second balance, a titrant reservoir resting on the balance, and a titration means comprising a potentiometric electrode, a stirring means, and a titration cup for containing the solution to be titrated. The second balance accurately weighs the amount of titrant added to the solution to be titrated. Control means connected to the first and second balances receives weight determinations from the first and second balances and uses the weight determinations to gravimetrically determine the concentrations of the primary standard solution, the titrant, the iodine solution, and the supernatant iodine solution. The control means calculates the iodine adsorption number of the carbon black based on the concentration determinations.

In the present invention, an appropriate titrant known to those skilled in the art as being useful for titrating iodine solution is used. A preferred titrant comprises sodium thiosulfate solution.

An appropriate primary standard is used to standardize the titrant. Such primary standards include but are not limited to potassium iodate, potassium biiodate, potassium chromate, potassium dichromate, potassium bromate, sodium bromate, potassium hexacyanoferrate (III), N-bromosuccinimide, dichromate with ethylenediamine tetraacetate (EDTA), or the like. Potassium biiodate is preferred.

In another embodiment of the present invention, the concentration of the iodine solution is determined by adding the same to an accurately weighed portion of a primary standard solution comprising arsenic oxide of a known concentration. The standardized iodine solution is then used to standardize the sodium thiosulfate titrating solution by adding the sodium thiosulfate solution to an accurately weighed portion of the standardized iodine solution until an endpoint is reached. The concentration of the sodium thiosulfate solution is then determined by accurately weighing the amount of the sodium thiosulfate solution necessary to reach the endpoint.

DETAILED DESCRIPTION

The gravimetric method of the present invention for determining the iodine adsorption number of carbon black comprises a number of steps which may be summarized as preparing the chemicals used in the method; standardizing the titrant; carrying out a blank determination of the iodine solution using the standardized titrant; and finally, determining the iodine adsorption number of the carbon black by equilibrating a weighed sample of the carbon black with iodine solution, and titrating the supernatant with the standardized titrant.

The gravimetric method of the present invention wherein sodium thiosulfate solution is the titrant and potassium biiodate is the primary standard is discussed in detail below.

A. Preparation of the Solutions

The chemicals used in the present invention are preferably analytical grade, and may be prepared according to any method known to those skilled in the art. Alternatively, certain of these chemicals may be obtained as pre-mixed solutions from approved commercial sources. The gravimetric method of the present invention preferably uses iodine and sodium thiosulfate solutions prepared in the same manner as in the volumetric method set forth in ASTM D1510.

The solutions needed to carry out the gravimetric analysis include a solution of sodium thiosulfate, a solution comprising potassium biiodate, for example, for standardizing the sodium thiosulfate solution, and iodine solution. In the following example, a mixture of 10% potassium iodide, potassium biiodate, and 10% sulfuric acid solution are used in the standardization of the sodium thiosulfate solution and are prepared as follows.

A solution of sodium thiosulfate ($0.0394 \pm 0.0002$ moles/kg) may be prepared, for example, by adding about 4 liters of water, 156.5 g of sodium thiosulfate and 80 ml of n-amyl alcohol to a calibrated vessel and stirring until the crystals dissolve. Thereafter, a sufficient quantity of water is added to make a total of 16 liters with stirring for 1–2 hours After aging the solution for 1–2 days, the solution is ready for use after stirring for ½ hour.

A solution of 10% potassium iodide (KI) solution may be prepared, for example, by weighing 10 g of potassium iodide into a small stoppered flask or bottle and then adding enough water to bring the total volume to 100 ml using distilled deionized water.

The potassium biiodate solution may be prepared, for example, as follows. Four grams of potassium biiodate are dried for 1 hour at 125° C., and then allowed to cool to ambient temperature in a desiccator for 15 minutes. A polyethylene container is tared on a balance. Next, between about 1–1.1 g of potassium biiodate is added to the container and accurately weighed, and then 150 g of distilled deionized water is added and accurately weighed. The container is stoppered and shaken horizontally for a minimum of about 15 minutes on a mechanical shaker.

The concentration of the potassium biiodate solution is determined according to the following formula:

$$\text{concentration of potassium biiodate (moles/kg)} = \frac{\text{weight of potassium biiodate} \times 2.5645}{\text{weight of resulting solution}}$$

where 2.5645 is the stoichiometric and scaling factor (to bring the units into proper alignment).

A 10% solution of sulfuric acid may be prepared, for example, by diluting 10 ml of concentrated sulfuric acid to 100 ml using distilled deionized water.

A 1% soluble starch solution may be prepared, for example, by adding 1 g of starch to 100 ml of boiling distilled deionized water. Thereafter, the water is boiled for two additional minutes, and the solution is cooled to room temperature. The solution is stable for about one week, or until precipitation occurs.

B. Standardization of the Sodium Thiosulfate Solution

First, about 5 ml of the potassium biiodate, is for example, added to a tared 100 ml titration cup and accurately weighed. Next, 10 ml each of the 10% potassium iodide solution and the 10% sulfuric acid solution are added, 25 ml of distilled-deionized water is added to the titration cup while washing down any drops on the walls of the cup.

The contents of the titration cup are then titrated against the sodium thiosulfate solution. The titration should begin not more than 2 minutes after the addition of the potassium iodide solution. The sodium thiosulfate is added gravimetrically until the solution turns light yellow, at which time about 5 drops of starch solution are added to the titration cup. The titration is then continued until a clear solution is obtained.

The concentration of the sodium thiosulfate solution is calculated as follows:

$$\text{concentration of sodium thiosulfate (moles/kg)} = \frac{\left(\text{concentration of potassium biiodate}\right) \times \left(\begin{array}{c}\text{weight of potassium} \\ \text{biiodate solution} \\ \text{used for} \\ \text{titration}\end{array}\right) \times 12}{\left(\text{mass of sodium thiosulfate at the titration endpoint}\right)}$$

where 12 is the stoichiometric factor.

Preferably, 2-3 separately prepared biiodate solutions are titrated for replicate determinations. The range of the replicate sodium thiosulfate concentration determination should preferably be less than $5 \times 10^{-5}$ moles/kg.

C. Blank Determination

Blank determinations of initial iodine concentrations are carried out using the standardized sodium thiosulfate solution.

Iodine solution ($0.02265 \pm 0.00015$ moles/kg) may be prepared, for example, according to the procedure set forth in ASTM D1510. Therein, 912 g of KI is accurately weighed and 700 g of it placed in a beaker and covered with sufficient distilled deionized water to dissolve it. The remaining KI is dissolved in two separate portions. Alternatively, any procedure which ensures that all of the KI is quantitatively dissolved is suitable. Thereafter, 96.0000 g $I_2$ is accurately weighed and added to the beaker. The weighing vessel and the funnel used to add the $I_2$ are washed with the remaining portions of the KI solution. Water is then added with stirring to make the total volume approximately 15 liters.

The blank determination may proceed as follows. Approximately 10 g of the iodine solution is dispensed into a flask and accurately weighed, 50 ml of deionized distilled water is then added to the iodine solution while rinsing the walls of the flask to ensure that all of the iodine is in the liquid phase and not on the sides of the flask. The iodine solution is then titrated with the standardized sodium thiosulfate solution. The titration may be done visually or colorimetrically. In this instance, the iodine solution is added until the solution is pale yellow. After adding 5 drops of starch solution, the titration is continued until the endpoint is reached, i.e., when the solution becomes colorless. In a preferred embodiment, the titration is carried out potentiometrically using a platinum electrode. The potential of the platinum electrode immersed in the iodine solution is continually determined. A rapid change in potential, or in other words maximum potentiometric changes versus the amount of thiosulfate added is obtained, and corresponds with the endpoint of the titration. The weight of the sodium thiosulfate solution necessary to reach the titration endpoint is then determined.

The concentration of the iodine blank is determined according to the following equation:

$$\text{concentration of iodine blank (moles/kg)} = \frac{\left(\text{concentration of sodium thiosulfate}\right) \times \left(\begin{array}{c}\text{weight of sodium} \\ \text{thiosulfate at} \\ \text{endpoint}\end{array}\right)}{\left(\begin{array}{c}\text{weight of iodine} \\ \text{solution used for} \\ \text{titration}\end{array}\right) \times 2}$$

where 2 is a stoichiometric factor.

The blank determination should be repeated 2-3 times. The relative standard deviation is preferably about 0.02% or less, and no trend should be observed.

D. Determination of the Iodine Number

An appropriate quantity of carbon black is dried for about one hour in an oven set at 125° C. The bed depth preferably should not exceed 0.25 inch. The dried carbon black is then placed inside a desiccator and cooled to room temperature.

The dried carbon black is weighed in an appropriate glass container which has been previously tared. Fluffy carbon blacks should preferably be densified before weighing, and most preferably before drying.

Alternatively to drying the carbon black, the weight of the carbon black can be determined from a sample of carbon black that contains a known amount of moisture. If the amount of moisture in the carbon black sample is known, the iodine adsorption number can be determined based on the calculated weight of the anhydrous carbon black.

The relationship of the weight of the moisture containing sample to the weight of anhydrous carbon black present may be determined as follows:

$$\left(\begin{array}{c}\text{weight of} \\ \text{carbon black} \\ \text{(anhydrous)}\end{array}\right) = \left(\begin{array}{c}\text{weight of} \\ \text{sample}\end{array}\right) - \frac{\left(\begin{array}{c}\text{percent} \\ \text{moisture in} \\ \text{sample}\end{array}\right)}{100} \times \left(\begin{array}{c}\text{weight of} \\ \text{sample}\end{array}\right)$$

Since the dried carbon black will absorb moisture once it is removed from the desiccator, it may be possible to further increase the precision of the iodine adsorption number by accounting for the moisture in the calculations rather than attempting to eliminate the moisture.

After the glass container containing the carbon black is accurately weighed, an appropriate amount of iodine is added. The amount of iodine which is to be added is based on the ratio used in the volumetric method of ASTM 1510, about 40 ml iodine per 0.8 g carbon black.

The carbon black-iodine mixture is then equilibrated by any method known to those skilled in the art. In one embodiment the carbon black-iodine mixture is equilibrated by shaking and centrifuging. More particularly, the glass container is shaken preferably on a conventional mechanical shaker set on "high". The mechanical shaker preferably is capable of providing a horizontal agitation of about 240 trips/minute. After shaking, the bottle is transferred to a centrifuge. Pelletized samples are preferably centrifuged for one minute while fluffy samples are preferably centrifuged for three minutes, when the centrifuge speed is set at about 2000 rpms (revolutions per minute).

Approximately 10 ml of the supernatant is transferred into a previously tared vessel (such as a 100 ml Mettler TM cup) and the supernatant is accurately weighed.

Next, 50 ml of deionized distilled water is added to the vessel, taking care to rinse the walls of the vessel to ensure that all of the iodine is in the liquid phase and not on the side walls of the vessel. The solution is then titrated with the standardized sodium thiosulfate solution. If the titration is carried out colorimetrically, the standardized sodium thiosulfate is added gravimetrically until the solution is pale yellow. The buret tip and walls of the vessel are washed with water, and 5 drops of starch solution added to the vessel. The titration is then resumed until the endpoint is reached, i.e., when the solution becomes colorless. Preferably, the titration is carried out potentiometrically using a platinum and reference electrode by adding the sodium thiosulfate solution gravimetrically until the titration endpoint is reached.

The weight of the sodium thiosulfate solution used to reach the endpoint of the titration is then determined. The concentration of the supernatant is determined as follows:

$$\text{concentration of iodine after equilibration with carbon black (moles/kg)} = \frac{\left(\begin{array}{c}\text{concentration of}\\\text{sodium thiosulfate}\\\text{solution}\end{array}\right) \times \left(\begin{array}{c}\text{mass of sodium}\\\text{thiosulfate solution}\\\text{at endpoint}\end{array}\right)}{\left(\begin{array}{c}\text{weight of iodine}\\\text{solution used for}\\\text{titration}\end{array}\right) \times 2}$$

where 2 is a stoichiometric factor

The iodine adsorption number is then determined as follows:

$$\text{Iodine number} = \frac{\left(\begin{array}{c}\text{concentration of}\\\text{iodine blank}\end{array} - \begin{array}{c}\text{concentration of}\\\text{iodine sample}\end{array}\right) \times \left(\begin{array}{c}\text{weight of iodine used}\\\text{with carbon black}\end{array}\right) \times 253.81}{\text{weight of carbon black}}$$

where 253.81 is the molecular weight of iodine

High purity water should be used in the method of the present invention. Thus, the water should be distilled and deionized. The conductivity of the water ideally should be less than 3 micromohs. Water ideally may be purified for use in the present invention, for example, by use of Nanopure System TM with 4 modules. The purified water can be stored in a container, but the container should be emptied and refilled once a day to ensure that no bacteria forms which would interfere with the titration.

The present invention as explained above may be carried out entirely manually. However, in a preferred embodiment for commercial applications, the present invention is modified such that it is carried out in semi-automated or fully-automated fashion.

In one such embodiment of the present invention, the gravimetric apparatus includes preparation means for weighing and otherwise for preparing the standardized solutions and other solutions to be titrated in order to obtain the iodine adsorption number. It comprises an iodine reservoir, a first Mettler TM balance, and equilibration means for equilibrating the carbon black-iodine mixture; and titration means which comprises a balance, means for elevating the Mettler TM balance, a sodium thiosulfate reservoir, a magnetic stirrer for stirring the iodine thiosulfate reaction mixture, a platinum and reference electrode and a titration cup which contains the solution to be titrated.

The Mettler TM balance of the preparation means is used for weighing iodine solution, carbon black, and, for example, potassium biiodate, and, for example, the potassium biiodate solution. The iodine reservoir contains iodine solution and is pressurized using an inert gas, preferably helium, for transferring iodine solution to a titration cup via tubing and a valve associated with the iodine reservoir. The valve is controlled by the operator, for instance via a toggle switch. The titration cup is placed on the balance where iodine solution is to be weighed, and iodine solution is transferred into the cup and weighed at the same time until the desired amount is obtained.

Alternatively, in another embodiment the iodine may be gravimetrically supplied via a dispensing device which uses a stepping motor or the like to dispense a given volume of iodine solution to the titrating cup. This embodiment is considered to be gravimetric because the dispenser is calibrated daily by dispensing a given volume of iodine solution, weighing the dispensed iodine solution, and calculating the density of the iodine solution based on the weight and volume measurements. Once the density is known, the correct volume of iodine solution (corresponding to a given weight) can be dispensed. One example of an acceptable dispensing device is the 665 Dosimet, available from Metrohm Corp.

The preparation means also include a means for equilibrating the carbon black-iodine mixture. In one embodiment, the means for equilibrating the carbon black-iodine mixture comprises a mechanical shaker and a centrifuge as previously discussed. In another embodiment, the equilibration may be accomplished by first stirring and then filtering the carbon black-iodine mixture. A portion of the filtrate is thereafter titrated with the standardized sodium thiosulfate solution. Stirring and filtering means are more suited to automation than shaking and centrifuging. For purposes of the present invention, the terms filtrate and supernatant are deemed to be synonomous.

While the temperature of the carbon black-iodine mixture is not as critical a parameter in the volumetric method, temperature becomes more important as the precision of the iodine adsorption number determination is improved. This is due to the fact that the adsorption of iodine onto carbon black is temperature dependent. As the temperature increases by 1° C., the adsorption of iodine onto the surface of carbon black decreases by approximately 0.1 mg/g. Thus, controlling the temperature is important in maintaining the precision of the gravimetric determination of the iodine adsorption number.

Accordingly, in another embodiment of the present invention, the temperature of the carbon black-iodine mixture is controlled by temperature controlling means. The temperature controlling means may comprise, for example, water baths into which the vessel containing the iodine solution to be added to the carbon black, and/or the vessel containing the carbon black-iodine mixture are placed. The temperature of the carbon black-iodine mixture can further be controlled more accurately in the embodiment where the mixture is subjected to stirring and filtration by placing these components in a water bath, etc. Alternatively, any other means for controlling the temperature of the carbon black-iodine mixture known to those skilled in the art can be used.

The balance of the titrating means includes a thiosulfate reservoir (i.e., a predetermined weight of sodium thiosulfate solution is contained in a vessel immediately prior to a given titration) and is used to measure the weight of sodium thiosulfate added to the solution being titrated. The thiosulfate reservoir is replenished upon completion of a given titration via tubing and a valve associated with a pressurized bottle containing sodium thiosulfate solution. The bottle is pressurized with an inert gas, preferably helium. The sodium thiosulfate solution from the thiosulfate reservoir on the balance is transferred to a titration cup containing the solution to be titrated via one or more tubing lines, each having an associated valve. Preferably, two tubing lines of varying diameter lead from the thiosulfate reservoir to the titration cup. The valves may be opened and closed via a toggle switch or by a computer, as explained infra. The larger diameter line is used for the initial parts of the titration, while the smaller diameter line is used for better accuracy when approaching the endpoint of the titration. The weight of the sodium thiosulfate solution transferred to the titration cup, as determined via the balance, is used to determine the concentration of the solution being titrated.

The means for elevating the balance in the titration station is useful in providing sufficient head pressure to yield an adequate flow rate of sodium thiosulfate from the thiosulfate reservoir to the titration cup. A platinum and reference electrode is associated with the titration cup, and may be held in place with a mechanical arm or the like.

Whenever the iodine reservoir or the bottle containing sodium thiosulfate solution are refilled or topped off, or the apparatus has not been used for eight hours or more, it is preferred that the associated lines, etc. be flushed with the appropriate solution.

In a preferred embodiment of the present invention, the gravimetric apparatus includes a control means such as a computer which is interfaced with the preparation means and the titration means. When the control means is a computer, it may be equipped with software which is designed to store all of the weights taken on the balance of the means and the balance of the titration means, perform the calculations necessary to obtain the iodine adsorption number, and/or control the valves in the lines carrying the standardized sodium thiosulfate solution to the titration cup. More particularly, the computer is interfaced with the balances of the preparation means and the balance of the titration means. The weight of each weighed sample is transferred by means of a hand key or the like. The computer is further interfaced with the platinum and reference electrode, the valves and the iodine dispenser. The software program is preferably designed to be user friendly. The computer and computer software allow the gravimetric method of the present invention to be conducted at a sufficient speed to render it both practical and preferable in commercial applications. This method improves the precision of the determination of the iodine adsorption number, which results in a decrease in the variability of the determination between laboratories and individuals, and also decreases the possibility of human error.

The computer software may be designed to allow the titration to proceed more accurately by controlling the opening and closing of the valve on the sodium thiosulfate line having the larger diameter and the valve on the smaller diameter line. For example, the titration can be controlled via computer prompts by which the valve to be opened is chosen and the time period (i.e., in tenths of seconds) that the valve is to be opened are selected.

The computer software may further be used to allow for additional aspects of the gravimetric method of the present invention to be automated.

For example, the computer software may include an algorithm which allows the automated determination of the potentionmetric titration endpoints. This may be accomplished by estimating the weight of sodium thiosulfate solution to be added to the solution being titrated without going past the titration endpoint. Yet adding enough in its titration does not take too long.

For example, the amount of standardized sodium thiosulfate solution to be added may be predicted from previously collected data points obtained during the potentiometric titration (i.e., milligrams thiosulfate solution added vs. millivolts) how much of the solution should be added with the next addition. This may be accomplished by predicting what the next derivative (incremental change in electrical potential divided by the incremental change in the weight of thiosulfate solution added) based on previous data, assuming equivalent additions of thiosulfate solution. By selecting an appropriate millivolt change, the amount of thiosulfate solution to be added can be calculated. The mass can be controlled for example, by the computer opening the valve on one of the two thiosulfate lines for a certain length of time, since the flowrate of each valve is predetermined.

One algorithm which is useful for predicting the derivative of the next point along the curve defining the relationship between electrical potential and total weight of sodium thiosulfate solution added is as follows:

$$\text{Average Predicted Derivative} = \frac{\left(\frac{\text{Der.}(J-1) + \text{Der.}(J-2) + \text{Der.}(J-G)}{G}\right)^2}{\left(\frac{\text{Der.}(J-2) + \text{Der.}(J-3) + \text{Der.}(J-i)}{i}\right)}$$

Where $J$ is defined as the data point to be predicted;

$G$ is the number of derivatives to be averaged; and $i = G + 1$.

The calculation of the derivative as set forth above continues as the computer compares newly calculated derivatives with previously calculated derivatives. The titration continues until a maximum derivative is reached, i.e. until the last-measured titration point provides a derivative which is less than the previously calculated derivative. Thereafter, the computer determines the exact titration endpoint by interpolating between the data point that has the maximum derivative and the points before and after. Preferably, after a derivative is obtained which is less than the previously calculated derivative, the titration is continued until a derivative is obtained which is a certain percentage smaller than the maximum (i.e., 60%) in order to eliminate the possibility of noise interfering with the maximum derivative and endpoint determinations. If this derivative is 60% or less of the maximum, the titration is stopped. Once the endpoint of the titration is determined, the aforementioned calculations for the iodine concentration of the supernatant and the iodine adsorption number of the carbon black can be carried out using the weights of the solutions and carbon black which are stored in the computer's memory.

The software may be further designed to carry out the density determination of the iodine solution when the iodine is dispensed from the dispenser rather than directly weighed. For example, the known volume of iodine solution dispensed and the weight of the same are transferred to the computer, which then performs the density calculation. Once the density of the iodine solution is known, the computer can determine the volume of the iodine solution to be dispensed by the dispenser based on the weight of the carbon black sample and accurately determine the weight of the iodine solution dispensed.

The computer may also be interfaced with other portions of the gravimetric apparatus of the present invention, including the temperature controlling means, the stirring means and the potential of the solution being titrated and the mass of sodium thiosulfate solution added, filtering means, and a printer for printing out data points such as derivatives thereof, elapsed time of the titration, flow rates, and results of calculations performed by the computer.

In another embodiment of the present invention, the computer is interfaced with a process control computer (commercially available or derived from commercially available programs) which controls the production of carbon black. Accordingly, the carbon black production parameters can be modified if the iodine adsorption number obtained is not within predetermined limits.

The accuracy at which weight determinations of the solutions are made in the present invention is about one magnitude (ten times) better than the accuracy of the volume determinations set forth in ASTM 1510. Moreover, the titrations of the present invention are about 5-10 times more accurate than by the volumetric method set forth in ASTM 1510. Overall, the improvement in precision of the measurements of the present invention is believed to be at least about three times better than the volumetric method. Thus, in order for the precision of the volumetric method to approach that of the present invention, the volumetric determination would have to be repeated nine times.

The software of the present invention may use the language Quick Basic TM from Microsoft Corporation, and the computer may be any commercially available conventional computer. The compiled code is used in combination with the instrumentation comprised of the control means and peripheral devices, because compiled code is faster than the interpreted mode and more transferable. The software controls the peripheral devices, collects data, stores data, analyzes data, reports results and provides a "user friendly" interface between the operator and the instrument.

The peripheral devices controlled by the software include the analytical and titrant balances for mass measurements, a platinum and reference electrode for voltage measurements, valves for controlling solution quantities delivered, a dispenser for precise automatic transfer of iodine solution, a printer for providing a hard copy of the raw data, analyzed data results, date, time and sample identification, and a monochrome monitor for displaying information to the operator.

The peripheral devices are interfaced to the computer specifications as follows. The balances and dispenser are interfaced to the computer by RS-232 hardware and software logic. The valves are interfaced to the computer using a data acquisition board placed in an expansion slot of the computer. This data acquisition board in this case transfers digital logic from the computer to relays which control the opening and closing of the respective valves. This operation controls the time the valves are open. The electrode is interfaced to the computer using the same data acquisition board mentioned above. In this case, the acquisition board converts the analog signal to a digital signal for use by the computer. The printer is interfaced to the computer using the parallel port of the computer. The monitor is interfaced to the computer using a video board in the expansion slot in the computer.

The data is collected by the computer by these interfaces where the data is subsequently stored. The software then analyzes the data for purposes of controlling the experiment and calculates the various parameters necessary to obtain an iodine number. The results are then transferred to a printer.

The following example will illustrate how the software interfaces with the devices and supplies a user friendly environment for the operator.

The operator interfaces to the instrument through a series of screen prompts. For example, one of the initial prompts in the program provides four options for the user. These options include determining the blank iodine concentration, determining the iodine number of a carbon black sample, standardizing thiosulfate solutions, and a help screen. For instance, if a user selects the iodine number option, the next series of prompts will guide the operator through these operations which will include weighing the carbon black, dispensing the iodine solution, and weighing and titrating an aliquot of the supernatant solution.

The weight of the carbon black is transferred directly to the computer by pressing a hand key attached to the balance. The quantity of iodine dispensed is calculated by the software and delivered either by a dispenser or gravimetrically with the aid of an operator controlled valve. The weight of the supernatant is also transferred directly to the computer with the balance hand key. The potentiometric titration is controlled by the software. Specifically the electrode voltage are measured and the open time of the valves are controlled in such a way so that the endpoint of the titration is correctly reached without operator involvement.

The software then determines the endpoint by using the maximum derivative technique. The concentration of the iodine solution is then determined from the weight of the iodine solution used for the titration and the endpoint mass of the thiosulfate solution. The iodine number is then calculated from the previously determined iodine blank concentration, iodine sample concentration and weights of carbon black and iodine solution equilibrated with the carbon black.

The examples provided above are not meant to be exclusive. Many other variations of the present invention would be obvious to those skilled in the art. For example, it may be possible to use the present invention for gravimetrically determining the iodine adsorption number of other carbonaceous materials such as graphite and charcoal, and other substrates such as platinum, magnesium oxide, glass spheres, alumina, and silica. All such obvious modifications are contemplated to be within the scope of the appended claims.

I claim:

1. An apparatus for gravimetrically determining the iodine adsorption number of carbon black, comprising
   preparation means for preparing iodine solution, carbon black, an appropriate primary standard, and a solution comprising said primary standard for titration against an appropriate titrant, said preparation means including a first balance for weighing said iodine solution, said carbon black, said primary standard, and said solution comprising said primary standard, and equilibration means for equilibrating a mixture of accurately weighed carbon black and accurately weighed iodine solution,
   titration means for titrating said primary standard solution, said iodine solution, and supernatant obtained from an equilibrated mixture of said carbon black and said iodine solution against said titrant, said titration means comprising a second balance, a titrant reservoir resting on said second balance, an indicating and reference electrode, a magnetic stirrer, and a titration cup for containing the solution to be titrated, said second balance accurately weighing the amount of titrant added to said primary standard solution, said iodine solution, and said supernatant, and
   control means connected to said first and second balances, said control means receiving weight determinations from said first and second balances and using said weight determinations to gravimetrically determine the concentrations of said primary standard solution, said titrant, said iodine solution, and said supernatant, said control means calculating the iodine adsorption number of said carbon black based on said concentration determinations.

2. The apparatus of claim 1, wherein said titration means further comprises a first and a second transferring means for transporting said titrant from said titrant reservoir to said titration cup, said first transferring means transporting said titrant to said titration cup at a faster rate than said second transferring means, a first valve for controlling the flow of said titrant solution through said first transferring means, a second valve for controlling the flow of said titrant through said second transferring means, and control means adapted to open and close said first and second valves during said titration of said primary standard solution, said iodine solution, and said supernatant.

3. The apparatus of claim 1, wherein said control means is adapted to predict the weight of said titrant needed to reach titration endpoints by comparing the derivatives of previously collected data points during a titration.

4. The apparatus of claim 1, wherein said equilibration means comprises shaking means and a centrifuge for shaking and centrifuging said carbon black-iodine solution mixture.

5. The apparatus of claim 1, wherein equilibration means comprises stirring means and filtration means for stirring and filtering said carbon black-iodine solution mixture.

6. The apparatus of claim 1, wherein said preparation means further comprises dispensing means for accurately and directly adding said iodine solution to said carbon black, said control means calibrating said dispensing means based on the weight of said iodine solution.

7. The apparatus of claim 1, wherein said preparation means further comprises temperature control means for controlling the temperature of said carbon black-iodine solution mixture.

8. The apparatus of claim 1, further comprising a process control means for controlling process parameters in the manufacture of carbon black, said process control means adapted to receive said calculation of said iodine adsorption number from said control means and adjust one or more of said process parameters if said iodine adsorption number is outside a predetermined limit.

9. The apparatus of claim 1, wherein said indicating electrode is a platinum electrode.

* * * * *